(12) United States Patent
Rackow et al.

(10) Patent No.: US 10,206,633 B2
(45) Date of Patent: Feb. 19, 2019

(54) METHOD FOR PLANNING SUPPORT AND COMPUTER TOMOGRAPHY DEVICE

(71) Applicant: Siemens Aktiengesellschaft, Munich (DE)

(72) Inventors: Bastian Rackow, Erlangen (DE); Stefan Reichelt, Bamberg (DE); Carsten Thierfelder, Pinzberg (DE)

(73) Assignee: Siemens Aktiengesellschaft, Munich (DE)

( * ) Notice: Subject to any disclaimer, the term of this patent is extended or adjusted under 35 U.S.C. 154(b) by 111 days.

(21) Appl. No.: 14/425,767

(22) PCT Filed: Sep. 5, 2013

(86) PCT No.: PCT/EP2013/068338
§ 371 (c)(1),
(2) Date: Mar. 4, 2015

(87) PCT Pub. No.: WO2014/044540
PCT Pub. Date: Mar. 27, 2014

(65) Prior Publication Data
US 2015/0208989 A1 Jul. 30, 2015

(30) Foreign Application Priority Data

Sep. 20, 2012 (DE) .......................... 10 2012 216 850

(51) Int. Cl.
*A61B 6/00* (2006.01)
*A61B 6/03* (2006.01)
(Continued)

(52) U.S. Cl.
CPC ................ *A61B 6/032* (2013.01); *A61B 6/03* (2013.01); *A61B 6/0492* (2013.01); *A61B 6/461* (2013.01);
(Continued)

(58) Field of Classification Search
CPC ....... A61B 6/544; A61B 6/0492; A61B 6/542; A61B 6/032; A61B 6/08; A61B 2090/366; A61B 90/36
See application file for complete search history.

(56) References Cited

U.S. PATENT DOCUMENTS 4,538,289 A * 8/1985 Scheibengraber ..... A61B 6/032
378/20
5,572,568 A 11/1996 Kanemitsu
(Continued)

FOREIGN PATENT DOCUMENTS

CN 101036584 A 9/2007
CN 101072540 A 11/2007
(Continued)

OTHER PUBLICATIONS

International Search Report dated Feb. 21, 2014.
(Continued)

*Primary Examiner* — David J Makiya
*Assistant Examiner* — Soorena Kefayati
(74) *Attorney, Agent, or Firm* — Harness, Dickey & Pierce, P.L.C.

(57) ABSTRACT

An embodiment of the invention relates to a method for planning support for a computer tomography recording of an examination object by means of a computer tomography device, including the following steps: recording a 2-D overview image (topogram) of the examination object by means of the computer tomography device, determining position-dependent information by means of the overview image, forwarding the information to a projection device, and correct positioned displaying the information on the surface of the examination object.

5 Claims, 1 Drawing Sheet

Figure 1:
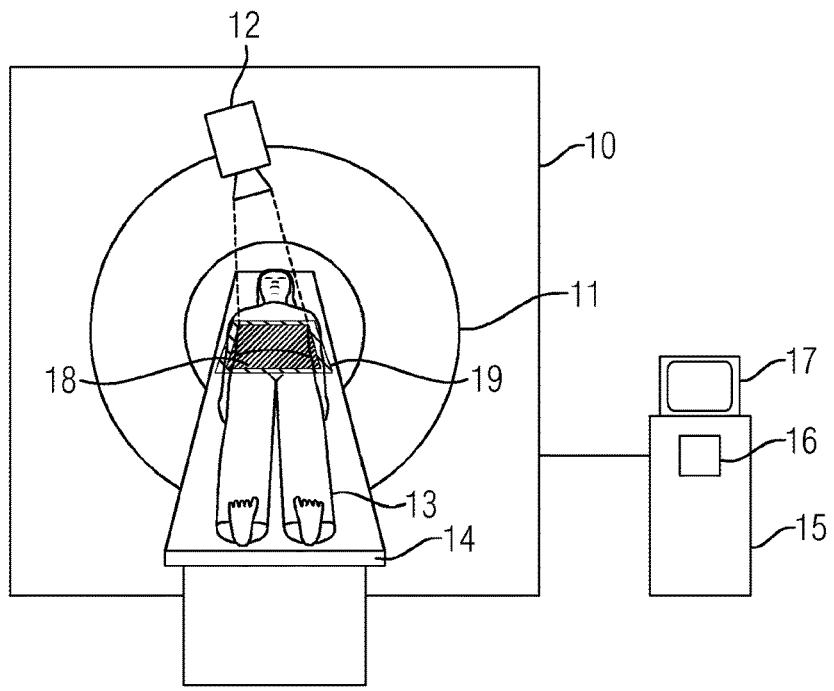

(51) Int. Cl.
  *G06T 11/00*  (2006.01)
  *G06T 7/00*   (2017.01)
  *G06T 7/73*   (2017.01)
  *A61B 6/04*       (2006.01)
  *A61B 90/00*      (2016.01)

(52) U.S. Cl.
  CPC .............. *A61B 6/488* (2013.01); *A61B 6/544* (2013.01); *G06T 7/74* (2017.01); *G06T 11/005* (2013.01); *A61B 6/0407* (2013.01); *A61B 2090/366* (2016.02); *G06T 2207/10072* (2013.01)

(56) References Cited

U.S. PATENT DOCUMENTS

| | | | | |
|---|---|---|---|---|
| 5,577,095 | A * | 11/1996 | Kobayashi | A61B 6/032 378/205 |
| 5,673,300 | A | 9/1997 | Reckwerdt et al. | |
| 6,865,254 | B2 * | 3/2005 | Nafstadius | A61N 5/1049 378/4 |
| 7,433,503 | B2 * | 10/2008 | Cherek | A61B 5/0555 378/4 |
| 7,465,090 | B2 * | 12/2008 | Haras | A61B 6/08 378/206 |
| 7,583,781 | B2 * | 9/2009 | Wakai | A61B 6/032 378/147 |
| 7,600,434 | B2 * | 10/2009 | Bak | A47C 31/123 73/849 |
| 7,632,015 | B2 * | 12/2009 | Stayman | A61B 6/032 378/163 |
| 7,697,147 | B2 * | 4/2010 | Kindlein | A61B 6/08 356/601 |
| 8,002,465 | B2 * | 8/2011 | Ahn | A61B 6/04 378/20 |
| 8,083,389 | B2 * | 12/2011 | Helmreich | A61B 5/055 362/253 |
| 8,235,530 | B2 * | 8/2012 | Maad | A61B 6/0407 250/492.1 |
| 8,995,611 | B2 * | 3/2015 | Durgan | A61B 6/032 378/20 |
| 9,050,058 | B2 * | 6/2015 | Uebayashi | A61B 6/54 |
| 9,060,740 | B2 * | 6/2015 | Lindenberg | G01B 11/25 |
| 2003/0068005 | A1 * | 4/2003 | Yamazaki | A61B 6/032 378/4 |
| 2005/0254616 | A1 * | 11/2005 | Nakanishi | A61B 6/032 378/4 |
| 2006/0235849 | A1 | 10/2006 | Frielinghaus | |
| 2007/0189456 | A1 | 8/2007 | Haras | |
| 2009/0141854 | A1 | 6/2009 | Hirokawa et al. | |
| 2009/0163809 | A1 | 6/2009 | Nohara | |
| 2009/0175518 | A1 * | 7/2009 | Ikuma | A61B 5/06 382/128 |
| 2009/0180590 | A1 * | 7/2009 | Borgmann | A61B 6/00 378/97 |
| 2010/0020923 | A1 * | 1/2010 | Fukano | A61B 6/032 378/19 |
| 2010/0177867 | A1 * | 7/2010 | Kozelj | A61B 6/035 378/20 |
| 2011/0142196 | A1 * | 6/2011 | Shinno | A61B 6/032 378/20 |
| 2012/0253200 | A1 | 10/2012 | Stolka et al. | |
| 2013/0016185 | A1 | 1/2013 | Stolka et al. | |
| 2014/0241511 | A1 * | 8/2014 | Hausotte | A61B 6/08 378/206 |
| 2014/0348296 | A1 * | 11/2014 | Goossen | A61B 6/0492 378/62 |

FOREIGN PATENT DOCUMENTS

| | | |
|---|---|---|
| CN | 101453952 A | 6/2009 |
| CN | 102090899 A | 6/2011 |
| JP | H07327984 A | 12/1995 |
| JP | H1099456 A | 4/1998 |
| JP | 2006122479 A | 5/2006 |
| JP | 2006122479 A | 5/2006 |
| WO | WO-11063266 A2 | 5/2011 |
| WO | WO 2011063266 A2 | 5/2011 |
| WO | WO-2011071442 A1 | 6/2011 |

OTHER PUBLICATIONS

German Office Action dated Mar. 28, 2013.
International Search Report PCT/ISA/210 for International Application No. PCT/EP2013/068338 dated Feb. 11, 2014.
Written Opinion of the International Searching Authority PCT/ISA/237 for International Application No. PCT/EP2013/068338 dated Feb. 11, 2014.
Chinese Office Action dated Oct. 10, 2016 issued in corresponding Chinese Application No. 2013800485260 (with translation).
Korean Notice of Allowance dated Oct. 5, 2016 issued in corresponding Korean Application No. 9-5-2016-071737479.
Chinese Office Action corresponding to Chinese Application No. 2013800485260 dated Apr. 24, 2017.

* cited by examiner

METHOD FOR PLANNING SUPPORT AND COMPUTER TOMOGRAPHY DEVICE

The invention relates to a method for planning support for a computer tomography recording as claimed in claim 1 and to a computer tomography device for carrying out a method of this kind as claimed in claim 8.

Fundamental components of a computer tomography device are a circular gantry having a recording system, in which gantry the examination object (for example the patient) is positioned by means of an examination table; a system controller for controlling the computer tomography device and at least one arithmetic unit (for example a computer). A large number of slice images in a large number of angles of projection around the examination object are recorded by means of the recording system, which has for example a single- or multi-line detector in fan geometry and an X-ray source, and are then reconstructed by means of the arithmetic unit, for example to form a 3D volume image, and then reworked if necessary.

Before recording the projection images, which is also associated with a higher X-ray dose and should therefore not be repeated several times, in order to plan the execution of the image recording it is important for a user to obtain more accurate information, for example which region exactly should be scanned or may be scanned at all, how much dose should be applied, etc. A conventional method in clinical practice is therefore to record a 2D overview image first of all. In the case of a computer tomography examination this pre-recording is called a topogram. In order to obtain a topogram the examination object arranged on the examination table is conventionally moved through the gantry of the computer tomography device along an axis, given by the longitudinal direction of the positioning means. Projections are continuously recorded without rotation of the recording system, and these are then made available to an arithmetic and control unit, for example a computer. The projections are interpolated in the arithmetic and control unit to form an overview image similar to an X-ray superposition image. The topogram is frequently recorded from the direction a.p. (anterior to posterior), p.a. (posterior to anterior) or laterally (from left to right or from right to left), depending on the desired image depiction.

The examination is then planned using this overview image, which is displayed on a monitor. Scannable travel ranges, known as scan ranges, are illustrated here. These scan ranges are then illustrated on the topogram as boxes. Information relating to the dose distribution is also displayed as a curve in addition to the topogram.

It is an object of the present invention to provide a method which enables particularly simple planning of a computer tomography recording in relation to its exact position. It is a further object of the invention to provide a computer tomography device capable of carrying out the method.

The object is achieved according to the invention by a method for planning support for a computer tomography recording as claimed in claim 1 and by a computer tomography device as claimed in claim 8. Advantageous embodiments of the invention are the subject matter of the associated subclaims in each case.

The inventive method for planning support for a computer tomography recording of an examination object by means of a computer tomography recording device comprises the following steps:

recording a 2D overview image (topogram) of the examination object by means of the computer tomography device, determining position-dependent information by means of the overview image, forwarding the information to a projection device, and correct positioned displaying of the information on the surface of the examination object.

To plan execution for example of a 3D image recording, a 2D overview image, what is known as a topogram, is recorded by means of CT. The topogram represents an overview of the patient and his anatomy. During the recording thereof the recording system is not rotated and instead the patient volume travels only in an axial direction for example. A superposition image similar to a conventional X-ray image is obtained in the process. Position-dependent information is taken to mean data which is determined by using the topogram (and if required additional information from the CT) and can apply to specific positions or regions of the examination object. Therefore scannable travel ranges (scan ranges) can in particular be determined which can be reached and recorded by means of the recording system of the CT, or the non-scannable edge regions can be ascertained.

The position-dependent information is forwarded to a projection device which can be part of the computer tomography device, and is superimposed by the projection device so as to be correctly positioned on the surface of the examination object. Correct positioned displaying directly on the surface of the examination object concerned therefore shows a user the exact information very clearly, so an incorrect presentation to the user(s) of the actual arrangement is virtually ruled out. The error rate in planning can be reduced thereby. The user (s) is/are given the opportunity to influence the recordings early on, so superfluous recordings can be prevented and the examination can be made safer for the patient.

A computer tomography device is provided for carrying out the method, having a rotatable gantry with a recording system for recording projected images from various directions of projection, an examination table for positioning an examination object, a system controller for controlling the computer tomography device, an arithmetic unit for processing and reconstructing the projected images and a projection device for projecting a photographic image onto a surface, wherein the system controller is adapted to forward information ascertained from an overview image of the examination object to the projection device, and the projection device is arranged in such a way that it projects the information correctly positioned, onto the surface of the examination object.

According to one embodiment of the invention the projection device is arranged on the gantry of the computer tomography device. Simple and unhindered projection of a photographic image onto the examination object is possible in this way even when it is arranged inside the gantry. Registration between the projection device and the recording system of the CT is also facilitated in this way.

According to a further embodiment of the invention the projection device is formed by a light projector. A light projector of this kind is commercially obtainable and can be used for the computer tomography device with little expenditure. Multi-color and single-color projections may also be created. Alternatively, a laser projector or a holographic projector for example may also be used.

According to one embodiment of the invention additional data is used to ascertain the position-dependent information, for example data on the geometry of the computer tomography device or its recording system, the recording parameters of the topogram or planned 3D recordings, information on the patient or the dimensions of the examination table.

According to a further embodiment of the invention further additional information of the computer tomography device is displayed on the surface of the examination object, for example outside of the regions onto which the position-dependent information is projected. A dose distribution curve for example can therefore be displayed.

According to one embodiment of the invention the display is projected onto the examination object in different colors. Therefore, scan ranges can be displayed in green and non-scannable ranges in red for example, or various possible scan ranges can be displayed in different colors. Measuring errors or regions of the topogram not recorded can also be displayed marked in color.

According to a further embodiment of the invention planning of a computer tomography recording is carried out on the basis of the information displayed on the surface of the examination object. The scan ranges for a computer tomography recording are selected automatically for example for this purpose.

Figure 2:
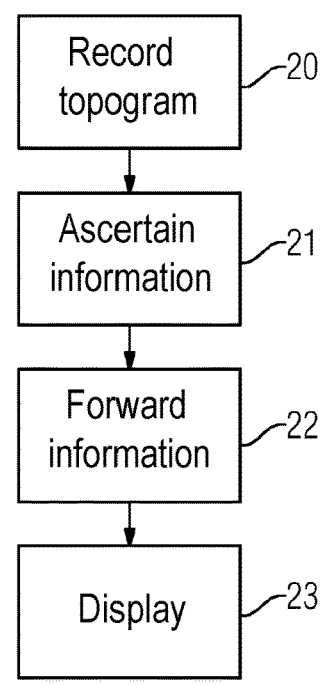

The invention and further advantageous embodiments according to features of the subclaims will be explained in more detail in the drawings below using schematically illustrated exemplary embodiments, without this limiting the invention to these exemplary embodiments. In the drawings:

FIG. 1 shows a view of an inventive computer tomography device having a light projector and FIG. 2 shows a sequence of an inventive method.

FIG. 1 shows an inventive computer tomography device 10 having a light projector 12. The computer tomography device 10 has a gantry 11 which comprises a line detector (not shown) and an X-ray source. The gantry 11 is able to be rotated around an opening in which a patient 13 arranged on an examination table 14 is positioned. The computer tomography device 10 also has a system controller 15 which is provided for controlling the device. An arithmetic unit 16 and a display unit, for example a monitor 17, are also provided. The arithmetic unit is designed for calculating and reconstructing X-ray images and can be integrated in the system controller 15. The system controller 15 and the arithmetic unit 16 can be formed for example by a computer. The light projector 12 is arranged above the examination table, for example on or in the gantry 11 or on a holding device, for example on a ceiling of an examination room, and is also controlled by the system controller. The light projector 12 is adapted to project correctly positioned information in one or more colors onto the surface of the patient. This information can be formed for example by the scan range 18 or the non scannable range 19. The ranges can be projected onto the surface of the patient for example as rectangles or other geometric shapes. The computer tomography device is adapted to carry out the inventive method automatically.

FIG. 2 shows a sequence of the inventive method. In a first step 20 a 2D overview image (topogram) is recorded by means of the computer tomography device. The patient 13 arranged on the examination table 14, for example, is in the process moved through the gantry along an axis, given by the longitudinal direction of the examination table. Projections are recorded continuously without rotation of the recording system, and these are then interpolated in the arithmetic unit to form the topogram. Position-dependent information is then ascertained in a second step 21 using data from the overview image, for example the scannable and/or non-scannable travel ranges (scan ranges). This can be carried out for example by means of the system controller and/or the arithmetic unit 16.

The position-dependent information is then transferred in a third step 22 to the light projector and projected correctly positioned by this in a fourth step 23 onto the patient or the surface thereof by means of the light projector. The corresponding scan ranges are therefore displayed, for example by colored rectangles or other geometric shapes, on the surface of the patient and, more precisely, in the exact position which was previously determined by means of the topogram. In addition, the non-scannable ranges for example are superimposed for example in a further color different from the first color. Further information may also be superimposed onto the surface of the patient, moreover, for example a dose distribution curve or the recording mode used. These do not have to be superimposed correctly positioned. In addition, errors or non-scannable ranges for example may be displayed or corresponding areas can be illuminated on the patient.

Within the scope of the invention information about the topogram, for example the ranges that can be scanned or cannot be scanned, is displayed directly on the patient and therefore very clearly. One application is for example a trauma patient who is being prepared for an examination. Normally a lot of involved physicians stand around the examination table before the scan in order to attend to the patient. With an appropriate projection onto the surface of the patient all of those involved can clearly and unquestionably see at an early stage before the examination which scan ranges can be scanned or which ranges cannot be scanned.

The invention may be briefly summarized as follows: a method for planning support for a computer tomography recording of an examination object by means of a computer tomography device is provided for improved recording planning, having the following steps:
  recording a 2D overview image (topogram) of the examination object by means of the computer tomography device),
  determining position-dependent information by means of the overview image,
  forwarding the information to a projection device, and
  correct positioned displaying of the information on the surface of the examination object.

The invention claimed is:
1. A method for planning support for a computer tomography recording of an examination object via a computer tomography device, comprising:
  recording a 2D overview image of the examination object via the computer tomography device;
  determining a content of a projection image of the examination object;
  determining a position of the examination object;
  forwarding the projection image to a projection device; and
  displaying the projection image of the examination object on the surface of the examination object, the position of the projection image being consistent with the position of the object;
  wherein the determining a projection image of the examination object and the determining a position of the examination object are both based on the recorded 2D overview image; and
  wherein the determining a projection image of the examination object is an interpolation process;

wherein the projection image of the examination object includes a scannable range and a non-scannable scan range of the computer tomography device; and wherein the scannable range is marked in a first color and the non-scannable range is marked in a second color.

2. The method of claim 1, wherein additional data is used to determine the projection image of the examination object.

3. The method of claim 1, wherein additional information of the computer tomography device is also displayed on the surface of the examination object.

4. The method of claim 1, wherein planning of a computer tomography recording is carried out on the basis of the projection image of the examination object displayed on the surface of the examination object.

5. A method for planning support for a computer tomography recording of an examination object via a computer tomography device, comprising:

recording a 2D overview image of the examination object via the computer tomography device;

determining a content of a projection image of the examination object;

determining a position of the examination object;

forwarding the projection image to a projection device;

displaying the projection image of the examination object on the surface of the examination object, the position of the projection image being consistent with the position of the object;

wherein the determining a projection image of the examination object and the determining a position of the examination object are both based on the recorded 2D overview image; and wherein the determining a projection image of the examination object is an interpolation process; and wherein the projection image of the examination object includes a scannable range and a non-scannable scan range of the computer tomography device; and wherein the scannable and non-scannable ranges are marked in different colors.

* * * * *